United States Patent
Feit

(12) 
(10) Patent No.: US 7,100,476 B1
(45) Date of Patent: Sep. 5, 2006

(54) TORQUE WRENCH FOR DENTAL IMPLANTS

(76) Inventor: Steven H. Feit, 3215 NW. 63rd St., Boca Raton, FL (US) 33496

( * ) Notice: Subject to any disclaimer, the term of this patent is extended or adjusted under 35 U.S.C. 154(b) by 0 days.

(21) Appl. No.: 11/345,476

(22) Filed: Feb. 1, 2006

(51) Int. Cl.
 *B25B 17/00* (2006.01)
 *A61C 3/00* (2006.01)

(52) U.S. Cl. .................. 81/57.29; 81/57; 81/57.14; 81/57.16; 81/467; 81/468; 81/473; 433/114; 433/141; 433/147; 433/153

(58) Field of Classification Search ............ 81/57, 81/57.14, 57.29, 57.16, 467, 468, 473; 433/114, 433/141, 147, 153
See application file for complete search history.

(56) References Cited

U.S. PATENT DOCUMENTS 5,626,474 A * 5/1997 Kukla et al. ............... 433/141
6,786,725 B1 * 9/2004 Lustig et al. ............... 433/173

* cited by examiner

*Primary Examiner*—Lee D. Wilson
*Assistant Examiner*—Shantese McDonald
(74) *Attorney, Agent, or Firm*—Donald W. Meeker

(57) ABSTRACT

A manually-operated, adjustable dental implant torque wrench employs a screw holding sheath for placing a dental screw in a mouth of a patient. A handle offset to avoid opposite teeth to the work area is provided with a bevel gear and pinion set to translate the turning motion from a straight turning shaft in the handle to a perpendicular screw turning head. An assortment of replaceable snap-fit screw turning heads fits the various types of dental screws. An easy turn T-shaped handle with a pivotable turning knob is controlled by a torque limiting device.

6 Claims, 1 Drawing Sheet

TORQUE WRENCH FOR DENTAL IMPLANTS

CROSS-REFERENCE TO RELATED APPLICATIONS

Not Applicable.

STATEMENT REGARDING FEDERALLY SPONSORED RESEARCH OR DEVELOPMENT

Not Applicable. THE NAMES OF THE PARTIES TO A JOINT RESEARCH OR DEVELOPMENT

Not Applicable.

BACKGROUND OF THE INVENTION

1. Field of the Invention

The present invention relates to hand manipulated dental implements and particularly to a manually-operated and adjustable dental implant torque wrench which employs a bevel gear and pinion set, each of which is attached to a shaft, the bevel gear being attached through its shaft to a T-handle and the pinion gear is attached to the drive mechanism, said drive mechanism is located in an angled and offset head for accessibility to the patient's rear teeth and is equipped with a screw holding sheath.

2. Description of Related Art Including Information Disclosed Under 37 CFR 1.97 and 1.98

A dental implant, popularly known as a tooth implant, is an artificial root and tooth which are used to replace a missing tooth (or teeth). Dental implants are placed in the jaw to provide support for a dental restoration, fixed bridge or removable partial denture. Dental implants provide good chewing function and also improve the patient's cosmetic appearance thereby allowing the patient to smile, speak, and interact with others with greater confidence. The dental implants as well as other oral surgery involve dental screws which must be placed in line with threaded implanted screw receptacles and screwed into them to specific torque levels.

The mouth can only open so far. The average range of opening is between 40–50 mm. The average movement of the mandible (lower jaw) from side to side (right to left) is 7 mm. The average amount of mandible movement in a forward position is also about 7 mm. It is necessary to provide an instrument that will enable the clinician who is performing dental restorative (placing crowns, bridges or bars onto the implants once the bone has integrated and fused to the implants) procedures to:

bring screws to the mouth without dropping them in the throat area, to be able to access difficult areas of the back of the mouth and to be able to torque screws to the manufacturer's specifications.

To date there are no such item as a lock washer that can be placed on a screw that retains a crown or bridge to the dental implant. Every time the cycle of chewing is performed an impact moment is accomplished. Meaning, the teeth come together as if a hammer is hitting the head of a nail. The result is, the threads of the screw and the threads within the implant (the nut in this case) can disengage allowing the screw to back out and loosen. After many cycles of this impact moment occurring the screw can back out and the crown or bridge (teeth supported on the implant(s) become loose. Screws can fracture as a result making their retrieval potentially challenging. They can become wedged inside the implant body.

None of the prior art devices adequately address the problem of bringing the dental screws into the mouth and accurately positioning them for screwing into the implanted threaded socket, especially for the back area of the mouth.

U.S. Pat. No. 5,626,474, issued May 6, 1997 to Kukla, is for a manually operated dental implant torque wrench with an elongated shaft assembly having a first shaft end and a second shaft end. A manually operable control device is connected to the first shaft end of the elongated shaft assembly for rotating the elongated shaft assembly. An angled housing assembly having a passageway extending from a first open end of the housing to a second open end of the housing is provided. The housing has a first portion and a second portion in an angled relationship to the first portion. A drive assembly is provided within the passageway and is operatively connected to the elongated shaft assembly. The drive assembly includes a receptacle end rotatably mounted to the second open end and adapted for attaching a dental tool thereto. An adjustable torque limiting assembly is connected to the elongated shaft assembly for disengaging the elongated shaft assembly from rotation of the drive assembly when rotation of the elongated shaft assembly has reached an adjustable predetermined torque setting.

U.S. Pat. No. 6,162,053, issued Dec. 19, 2000 to Hollander, concerns an analog dental wrench with selectable adjustable torque-shear limits in which, at a given level of torque imparted to a dental work object, force communicated by a compression spring through an interface impart against a ball bearing will cause rotation of a handle and medial hollow cylindrical segment of the wrench off of the bearing to an off-axis position relative to a longitudinal work axis, disabling a wrench head, precluding further application of a torque to the work object, and causing shear of the wrench to occur either to the left or right of the longitudinal axis, and external to the mouth of the patient.

U.S. Pat. No. 5,337,638, issued Aug. 16, 1994 to Coss, illustrates an adjustable torque wrench for procedures requiring the application of precise small torques. The wrench includes a handle pivotally connected to a cam member rigidly attached to a driving head. The handle breaks out of alignment with the extending cam member upon application of an adjustable torque limit. A spring-biased plunger within the handle normally holds a rigid ball within an elliptical indent in the cam member. Application of the torque limit on the handle forces the ball out of the indent and onto an angled surface before a projecting flange of the handle contacts the cam member and limits the further pivot of the handle. The angled surface provides a reaction force to the ball sufficient to maintain the handle in a pivoted position. The handle pivots a noticeably large angle of 30.degree. before the flange contacts the cam member.

U.S. Pat. No. 4,680,994, issued Jul. 21, 1987 to Singleton, provides a speed socket wrench with a reversing ratchet, which substantially reduces the work required to remove nuts or bolts. The wrench includes a bevel gear and mating bevel pinion mounted respectively on a gear shaft and pinion shaft. A drive shaft is provided on the outer end of the pinion shaft. Interlocking cap elements are provided on the outer end of the drive shaft for releasably locking the drive shaft to prevent rotation thereof. In one embodiment, the cap elements include inner and outer caps which cooperate to provide a locking mechanism. In the locked position of the caps, the wrench can be employed as would any conventional wrench. In the unlocked position, a handle on the outer end of the gear shaft is rotatable by hand, resulting in revolving of the drive shaft. The gears of the present wrench turn freely in either direction and gear ratios and sizes can be varied with wrench size. In a further embodiment, a reversing ratchet mechanism is employed to lock the drive shaft.

U.S. Pat. No. 4,991,470, issued Feb. 12, 1991 to Singleton, shows a speed socket wrench with an improved handle which substantially reduces the work required to remove nuts or bolts. The wrench includes a bevel gear and mating bevel pinion mounted respectively on a gear shaft and pinion shaft. A drive shaft is provided on the outer end of the pinion shaft. A reversing ratchet mechanism is employed to lock the drive shaft. The specific construction and arrangement of components provides a socket wrench has been found to substantially reduce the work required to remove nuts or bolts, as compared with conventional wrenches. The present invention provides an improved T-handle for use with a tool having a shaft which rotates about its longitudinal axis. The T-handle is constructed with a generally L-shaped end member, having the shorter leg of the end member extending outwardly at an angle such as about 45 degrees and with the end member being pivotable at its center about the shaft so as to form an angle with the shaft which is complementary to the angle formed by the shorter leg of the end member with the main portion of the end member. In this manner, there is obtained a lever arm that is parallel to the shaft in the operating mode.

U.S. Pat. No. 4,262,561, issued Apr. 21, 1981 to Mize, claims a ratchet and gear drive socket wrench handle. An elongated handle is provided defining a hand grip at one end and an enlarged head at the other end. The enlarged head has a reversible ratchet-type drive assembly supported therefrom including a rotary output shaft disposed transverse to the handle. The handle is tubular intermediate the handle and head ends thereof and rotatably receives a torque input shaft extending therethrough. The torque input shaft and output shaft include meshed gear wheels and the end of the input shaft adjacent the hand grip includes first torque transfer structure. An elongated head is positioned adjacent and disposed transverse to the hand grip in alignment therewith and includes laterally projecting second torque transverse structure releasably coupled with the first torque transverse structure. The elongated head, on the side thereof remote from the head end of the handle, defines an elongated laterally opening groove formed therein and an elongated crank arm has one end pivotally mounted in one end of the groove for swinging of the crank arm between a retracted position within the groove and an extended position projecting endwise outwardly of the aforementioned one end of the groove. The other end of the crank arm includes a right angulated terminal end portion generally paralleling the handle when the crank arm is in both the retracted and extended positions.

U.S. Pat. No. 4,907,476, issued Mar. 13, 1990 to Singleton, describes a speed socket wrench with an improved handle which substantially reduces the work required to remove nuts or bolts. The wrench includes a bevel gear and mating bevel pinion mounted respectively on a gear shaft and pinion shaft. A drive shaft is provided on the outer end of the pinion shaft. A reversing ratchet mechanism is employed to lock the drive shaft. The specific construction and arrangement of components provides a socket wrench which has been found to substantially reduce the work required to remove nuts or bolts, as compared with conventional wrenches. The present invention provides an improved T-handle for use with a tool having a shaft which rotates about its longitudinal axis. The T-handle is constructed with a generally L-shaped end member, having the shorter leg of the end member extending outwardly at an angle such as about 45 degrees and with the end member being pivotable at its center about the shaft so as to form an angle with the shaft which is complementary to the angle formed by the shorter leg of the end member with the main portion of the end member. In this manner, there is obtained a lever arm that is parallel to the shaft in the operating mode.

U.S. Pat. No. 4,620,459, issued Nov. 4, 1986 to Singleton, discloses a speed socket wrench which substantially reduces the work required to remove nuts or bolts. The wrench includes a bevel gear and mating bevel pinion mounted respectively on a gear shaft and pinion shaft. A drive shaft is provided on the outer end of the pinion shaft. Interlocking cap elements are provided on the outer end of the drive shaft for releasably locking the drive shaft to prevent rotation thereof. In one embodiment, the cap elements include inner and outer caps which cooperate to provide a locking mechanism. In the locked position of the caps, the wrench can be employed as would any conventional wrench. In the unlocked position, a handle on the outer end of the gear shaft is rotatable by hand, resulting in revolving of the drive shaft. The gears of the present wrench turn freely in either direction and gear ratios and sizes can be varied with wrench size.

U.S. Pat. No. 2,703,030, issued Mar. 1, 1955 to Marvin, provides a manual gear-operated ratchet wrench that comprises a body having a bevel gear and pinion set, each of which is attached to a shaft. The bevel gear is attached through its shaft to a crank-type handle and the pinion set is attached to the drive mechanism.

U.S. Pat. No. 6,007,336, issued Dec. 28, 1999 to Sapkos, is for a dental prosthesis support device that can be positioned in a dental implant by mating screw threads with the support device being torqued to a predetermined torque, preferably using a torque wrench which can be set using a non-variable, preferably gravity-based, standard.

What is needed is an instrument that can carry a dental screw to a desired location anywhere in a mouth of a patient including in the back of the mouth without dropping it and can effectively turn the dental screw to the required torque level in all locations including the very rear of the mouth to allow greater confidence and ease of treatment when rendering procedures involving dental screws and provide the capability of being able to torque the screw to the desired torque level.

BRIEF SUMMARY OF THE INVENTION

An object of the present invention is to provide an instrument that can carry a dental screw to a desired location anywhere in a mouth of a patient including in the back of the mouth without dropping it and accurately align the dental screw with the threaded implant socket and with the screw turning head to effectively turn the dental screw to the required torque level in all locations including the very rear of the mouth to allow greater confidence and ease of treatment when rendering procedures involving dental screws and provide the capability of being able to torque the screw to the desired torque level.

Another object of the present invention is to provide various sizes and lengths to be adjusted to facilitate its use in the mouth for the application of implant dentistry and also orthopedic surgery for access to areas needing screw tightening or loosening as well as accommodating different mouth opening sizes.

One more object of the present invention is to provide an angled distal end of the dental implant wrench to avoid contact with the opposite set of teeth from the ones being worked on and to provide better visibility for working.

An additional object of the present invention is to provide a screw turning head which is perpendicular to the gripping handle to assist with accurate alignment of the screw turning head with the dental screw to screw it straight in to the threaded socket without stripping the threads or binding the screw.

A further object of the present invention is to provide a T-shaped handle with a pivotable turning assist knob for ease and accuracy of turning.

Yet one more object of the present invention is to provide replaceable screw turning heads with an assortment of working ends to fit the various types of dental screws commonly employed.

In brief, a manually-operated and adjustable dental implant torque wrench employs an elongated straight gripping handle with an angled offset at a distal end to accommodate the teeth opposite the teeth being worked on and provide better visibility to the work area. The screw turning head is attached to a distal end of the angled portion in a perpendicular orientation to the gripping handle for greater accuracy in placement and turning of the dental screws. A bevel gear and pinion set within the angled offset translates the turning motion of the shaft in the main gripping handle to the turning motion of the screw turning head. A T-shaped handle with a pivotally attached turning assist knob turns the main straight shaft in the gripping handle. A standard torque control is fit into the straight shaft section.

An array of changeable screw turning heads each alternately snap fit into the angled section of the implant torque wrench to fit the wide variety of types of dental screws in use.

A screw holding sheath grips the dental screw with a tight friction fit for placing the dental screw in the mouth and aligning it with the threaded implant socket. The sheath retracts or the screw turning head advances for screwing the dental screw in place when the screw is properly aligned.

An advantage of the present invention is that it provides an instrument that can carry a dental screw to a desired location anywhere in a mouth of a patient.

Another advantage of the present invention is that it provides accurate alignment of the dental screw with the threaded implant socket and with the screw turning head to insure accurate placement and screwing of the dental screws.

One more advantage of the present invention is that it provides the capability of being able to torque the screw to the required torque level.

Another advantage of the present invention is that it accommodates different mouth opening sizes and different dental procedures.

One more advantage of the present invention is that it avoids contact with the opposite set of teeth from the ones being worked on and provides better visibility for working.

A further advantage of the present invention is that it provides ease and accuracy of turning.

Yet one more advantage of the present invention is that it fits the various types of dental screws commonly employed.

BRIEF DESCRIPTION OF THE SEVERAL VIEWS OF THE DRAWINGS

These and other details of my invention will be described in connection with the accompanying drawings, which are furnished only by way of illustration and not in limitation of the invention, and in which drawings.

DETAILED DESCRIPTION OF THE INVENTION

Figure 1:
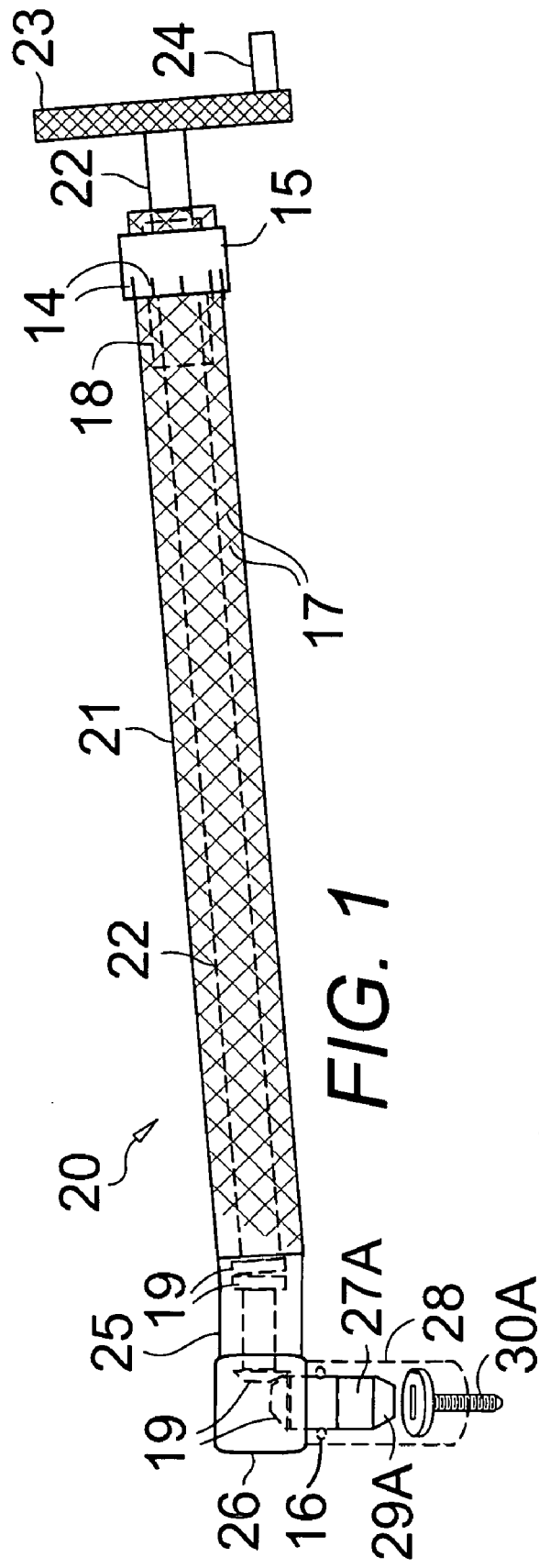
FIG. 1 is a side elevational view of the dental screw torque wrench of the present invention retaining a slotted dental screw in alignment with a slotted driver screw turning head.
Figure 2A:
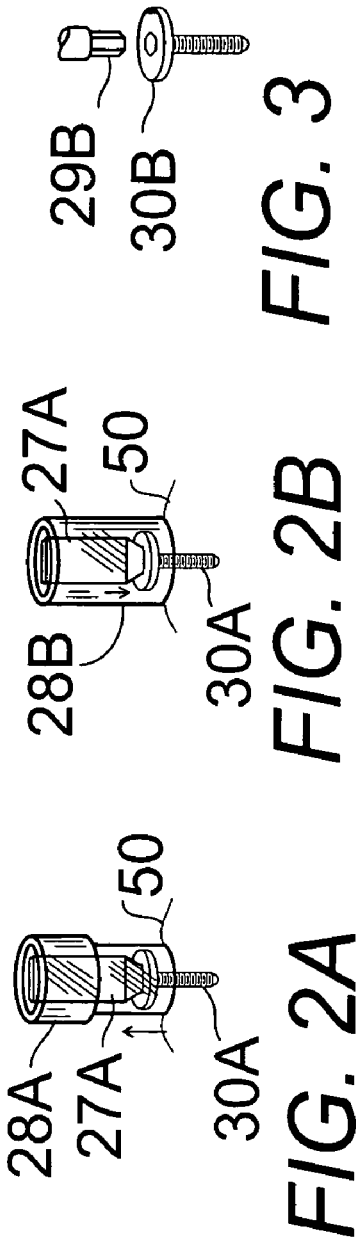
FIG. 2A is a partial perspective view of the screw turning head of FIG. 1 with a transparent telescoping screw retaining sleeve that moves relative to the screw turning head upon contacting the gums of the patient adjacent to the dental screw receiving area.
Figure 2B:
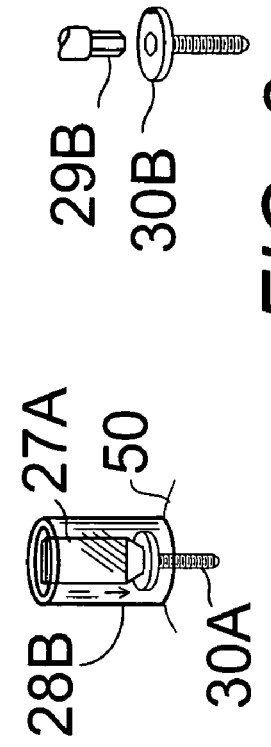
FIG. 2B is a partial perspective view of the screw turning head of FIG. 1 with a transparent immobile screw retaining sleeve and the screw turning head moves relative to the screw retaining sleeve down onto the dental screw when the screw retaining sleeve contacts the gums of the patient adjacent to the dental screw receiving area.
Figure 3:
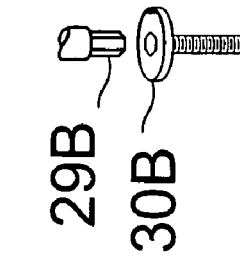
FIG. 3 is a partial perspective view of a hex head dental screw with a hex head driver screw turning head from the wrench of FIG. 1 aligned to turn the hex head screw.

In FIGS. 1–3, a torque wrench device 20 for dental implants comprises a straight gripping handle 21, T-shaped turning handle 23 with a pivotally attached turning assist knob, such as a gripping pin 24, an offset angled distal end 25, a replaceable screw turning head 27A, and a screw retaining sheath 28.

The dental implant torque wrench 20 comprises a gripping handle having an essentially horizontal elongated straight gripping portion 21 with a textured outer surface 17 for effective gripping in a wet mouth environment. An angled offset portion 25 at a distal end avoids contact with one set of the sets of upper and lower teeth while working on the other. The gripping handle having an interior passageway throughout the length of the gripping handle housing a rotatable shaft 22 in the straight gripping portion 21 of the gripping handle.

A rotatable handle 23 extends from the gripping handle 21 at a proximal end of the rotatable shaft for turning the rotatable shaft 22. The rotatable handle 23 has a standard means for controlling torque 18 in the handle with a knob 15 bearing indicia 14 to set the desired torque level to limit an amount of torque applied by the rotatable handle 23, which connects with the rotatable shaft 22. A turning facilitating element or knob 24 is rotatably attached to an end of one of the arms of the rotatable handle 23 for ease of turning with a single hand.

A screw turning head 27A extends from the angled offset portion 25 at the distal end of the gripping handle perpendicular to the gripping portion 21. The screw turning head 27A is preferably snap fit by a snap fitting means 16 such as a ring or movable sphere in a detante into the dental implant torque wrench for easy replacement. An assortment of replaceable screw turning heads, such as a slotted head 29A in FIGS. 1 and 2, a hex head 29B in FIG. 3, are provided each with different working ends to match a wide variety of different dental screws including slotted 30A, hex 30B, star, cross slotted, etc).

A bevel gear and pinion set 19 housed within the interior passageway in the angled offset portion 25 at the distal end of the gripping handle translates the pivotal motion of the rotatable shaft 22 to the screw turning head 27A for tightening and loosening dental screws 30A and 30B in a mouth of a patient.

In FIGS. 1, 2A and 2B, a screw gripping element, such as a screw retaining sheath 28, 28A and 28B, extends from the distal end of the gripping handle adjacent to the screw turning head 27A. The screw gripping element 28, 28A, and 28B is structured to retain a dental screw 30A for placing the dental screw in a proper location in a mouth of a patient and structured to release the dental screw in place in a mouth of a patient with the screw turning head contacting the dental screw. The screw gripping element preferably comprises a screw retaining sheath 28, 28A and 28B extending from the distal end of the gripping handle, the screw retaining sheath surrounding the screw turning head 27A and extending beyond an outer end of the screw turning head in a first position, as in FIG. 1, to retain a dental screw in the screw retaining sheath and the screw retaining sheath and screw turning head being movable relative to each other so that when the dental screw is positioned in a proper location in a mouth of a patient relative movement of the screw retaining sheath and the screw turning head leaves the screw turning head extending out beyond the screw retaining sheath in a second position, as in FIGS. 2A and 2B, to release a dental screw 30a with the screw turning head 27A contacting the dental screw so that the screw turning head is positioned to screw the dental screw into a desired location in a mouth of a patient with the rotatable handle 23 turning the screw turning head 27A through the rotatable shaft 22 and the bevel gear and pinion set 19 to screw in the dental screw 30A to a desired torque level.

In FIG. 2A, a telescoping transparent screw retaining sheath 28A is retractable and extensible relative to the screw turning head 27A as indicated by the arrow with the telescoping sheath pushed up by contact with the gums 50 of a patient.

In FIG. 2B, the screw retaining sheath 28B is a solid transparent cylinder secured to the handle and the screw turning head 27A is retractable and extensible relative to the screw turning head as indicated by the arrow so that when the sheath 28B contacts the gums 50 of the patient, the screw turning head 27A keeps moving down to contact the dental screw 30A.

The present invention is preferably fabricated of stainless steel or other sterilizable and durable material.

In use, a dentist or other medical professional inserts a dental screw 30A into the screw retaining sheath 28 and aligns the dental screw with a threaded implant socket in a mouth of a user. As the transparent sheath 28 contacts the gums 50 of a patient, the screw turning head 27A contacts the dental screw 30A, if not initially contacting the dental screw, and the dentist holds the gripping portion 21 of the handle in one hand and turns the T-shaped handle 23 by the gripping pin 24 to turn the screw turning head 27A to tighten the dental screw 30A to the required torque level.

It is understood that the preceding description is given merely by way of illustration and not in limitation of the invention and that various modifications may be made thereto without departing from the spirit of the invention as claimed.

What is claimed is:

1. A torque wrench device for dental implants comprising:
a dental implant torque wrench comprising a gripping handle having an elongated straight gripping portion and an angled offset portion at a distal end to avoid contact with one set of the sets of upper and lower teeth while working on the other, the gripping handle having an interior passageway throughout the length of the gripping handle, a rotatable shaft housed rotatably in the straight gripping portion of the gripping handle, a rotatable handle extending from the gripping handle at a proximal end of the rotatable shaft for turning the rotatable shaft, the rotatable handle having a means for controlling torque to limit an amount of torque applied by the rotatable handle, a turning facilitating element rotatably attached to the rotatable handle for ease of turning with a single hand, a screw turning head extending from the angled offset portion at the distal end of the gripping handle perpendicular to the gripping portion, a bevel gear and pinion set housed within the interior passageway in the angled offset portion at the distal end of the gripping handle, the bevel gear and pinion set translating pivotal motion of the rotatable shaft to the screw turning head for tightening and loosening dental screws in a mouth of a patient, a screw gripping element extending from the distal end of the gripping handle adjacent to the screw turning head, the screw gripping element structured to retain a dental screw for placing the dental screw in a proper location in a mouth of a patient and structured to release the dental screw in place in a mouth of a patient with the screw turning head contacting the dental screw, the screw gripping element comprising a transparent screw retaining sheath extending from the distal end of the gripping handle, the screw retaining sheath surrounding the screw turning head and extending beyond an outer end of the screw turning head in a first position to retain a dental screw in the screw retaining sheath and the screw retaining sheath and screw turning head being movable relative to each other so that when the dental screw is positioned in a proper location in a mouth of a patient relative movement of the screw retaining sheath and the screw turning head leaves the screw turning head extending out beyond the screw retaining sheath in a second position to release a dental screw with the screw turning head contacting the dental screw so that the screw turning head is positioned to screw the dental screw into a desired location in a mouth of a patient with the rotatable handle turning the screw turning head through the rotatable shaft and the bevel gear and pinion set to screw in the dental screw to a desired torque level.

2. The device of claim 1 wherein the rotatable handle comprises a T-shaped handle rigidly attached to the proximal end of the rotatable shaft with each of two ends of the T-shaped handle extending orthogonally from the rotatable shaft and the turning facilitating element rotatably attached to the rotatable handle comprises a gripping pin pivotally attached orthogonally to one end of the T-handle for gripping the gripping pin to turn the T-handle.

3. The device of claim 1 wherein the screw retaining sheath is retractable and extensible relative to the screw turning head.

4. The device of claim 1 wherein the screw turning head is retractable and extensible relative to the screw turning head.

5. The device of claim 1 further comprising a textured gripping surface around the straight gripping portion of the gripping handle to enable secure gripping under wet conditions during screw installation in a mouth of a patient.

6. The device of claim 1 wherein the screw turning head is snap fit into the dental implant torque wrench for easy replacement and an assortment of replaceable screw turning head are provided each with different working ends to match a wide variety of different dental screws.

* * * * *